US005783535A

United States Patent [19]
Isobe et al.

[11] Patent Number: 5,783,535
[45] Date of Patent: Jul. 21, 1998

[54] DETERGENT COMPOSITION COMPRISING AN AMIDOETHER DERIVATIVE MIXTURE AND A CONDITIONING COMPONENT

[75] Inventors: Kazuo Isobe; Toshikazu Azuma; Hideyo Nishikawa; Takashi Imamura, all of Wakayama-ken, Japan

[73] Assignee: Kao Corporation, Tokyo, Japan

[21] Appl. No.: 877,504

[22] Filed: Jun. 17, 1997

Related U.S. Application Data

[63] Continuation of Ser. No. 510,274, Aug. 2, 1995, abandoned.

[30] Foreign Application Priority Data

Aug. 2, 1994 [JP] Japan ................................. 6-181330

[51] Int. Cl.$^6$ ................. C11D 3/32; C11D 1/62; C11D 9/36; C11D 3/37
[52] U.S. Cl. ................. 510/126; 510/119; 510/501; 510/502; 510/235; 510/237; 510/123; 510/135; 510/503; 550/124; 550/130; 550/137; 514/852
[58] Field of Search ................. 514/852; 510/126, 510/501, 502, 235, 237, 119, 123, 135, 503; 550/124, 130, 137

[56] References Cited

U.S. PATENT DOCUMENTS

| | | | |
|---|---|---|---|
| 4,783,282 | 11/1988 | Smid | 252/546 |
| 4,818,440 | 4/1989 | Schafer et al. | 252/546 |
| 4,865,757 | 9/1989 | Singh-Verma et al. | 252/117 |
| 5,180,584 | 1/1993 | Sebag et al. | |
| 5,478,490 | 12/1995 | Russo et al. | 252/153 |

*Primary Examiner*—Paul Lieberman
*Assistant Examiner*—Charles Boyer
*Attorney, Agent, or Firm*—Oblon, Spivak, McClelland, Maier & Neustadt, P.C.

[57] ABSTRACT

The present invention relates to a detergent composition which comprises (A) an amidoether derivative mixture (A) comprising an amidoether carboxylic acid or a salt thereof, an amidoether, and a glycerin derivative; and (B) a conditioning component, wherein the total amount of the amidoether carboxylic acid or a salt thereof and the amidoether is 50 wt % or more; the weight ratio of the amidoether carboxylic acid or a salt thereof to the amidoether is from 99:1 to 10:90; and the amount of the glycerin derivative is 5 wt % or less.

11 Claims, No Drawings

DETERGENT COMPOSITION COMPRISING AN AMIDOETHER DERIVATIVE MIXTURE AND A CONDITIONING COMPONENT

This application is a Continuation of application Ser. No. 08/510,274, filed on Aug. 2, 1995, now abandoned.

BACKGROUND OF THE INVENTION

This invention relates to a detergent composition which hardly irritates the skin, exhibits excellent foaming properties, produces creamy foam, feels satisfactory to the touch during washing, and has excellent conditioning effects such as smooth touch of the skin or hair after washing.

Anionic surface active agents, such as alkylsulfates, polyoxyethylene alkylsulfates, alkylbenzenesulfonates, and α-olefin sulfonates, have widely been used in detergents because of their high foaming properties. However, these anionic surface active agents are more or less irritant to the skin and cause skin roughening when used continuously.

On the other hand, low-irritant surface active agents are known, such as alkyl saccharide type surface active agents, sulfosuccinic acid type surface active agents, ether carboxylic acid surface active agents, and amidoether carboxylic acid type surface active agents. However, the alkyl saccharide type surface active agents, though highly foaming, make hair squeak during washing or rinsing. To reduce the squeak of hair, a combined use with a conditioner such as a cationic polymer has been proposed as disclosed in Japanese Patent Application Laid-Open 2-42013, also U.S. Pat. No. 5,057,311, but it is not technically easy to incorporate a large quantity of such a conditioner into a shampoo. Since the sulfosuccinic acid type surface active agents alone have poor foaming properties, a combined use with other surface active agents has been suggested as disclosed in Japanese Patent Application Laid-Open 2-218797. In practice, they are often used in combination with other surface active agents. Commercially available ether carboxylic acid type or amidoether carboxylic acid type surface active agents also have poor foaming properties so that their utility, in those detergents of which high foaming properties are demanded, has been confined to use as auxiliary surface active agents.

The aforementioned amidoether carboxylic acid type surface active agents are commercially sold by Chem Y, Germany under a series of trade names "Akypo". The commercial products contain not only an amidoether carboxylic acid and the starting amidoether but also impurities such as polyoxyethylene glyceryl ether, polyoxyethylene glyceryl ether carboxylic acid and inorganic salts, which originates in the starting material.

Known techniques relating to application of amidoether carboxylic acid type surface active agents to detergents include a cosmetic composition comprising an amidoether carboxylic acid (European Patent 102118) also U.S. Pat. No. 4,818,440; a detergent composition obtained by combining an amidoether carboxylic acid surface active agent and a polyoxyethylene alkylsulfate (European Patent 215504); an amidoether carboxylic acid prepared from fat and oil and a detergent comprising the amidoether carboxylic acid (Japanese Patent Application Laid-open 63-291996 corresponding to European Patent 219893) also U.S. Pat. No. 4,783,282; and a detergent mainly comprising soap and having incorporated thereinto an amidoether carboxylic acid or an alkyl ether carboxylic acid salt (U.S. Pat. No. 4,865,757).

However, these conventional detergents are still unsatisfactory in foaming properties. Accordingly, it has been demanded to develop a detergent which is less irritant to the skin and excellent in foaming properties and also conditioning effects.

For example, it is known to incorporate a silicone or a silicone derivative into detergents in order to impart a gloss to hair and to smooth the surface of hairs for easy combing or to improve smoothness of the skin. However, incorporation of the silicone or the silicone derivative to a detergent reduces foaming properties.

Thus, none of the conventional detergent compositions containing a silicone or a silicone derivative is non-irritant to the skin and has high foaming properties while exhibiting the above-described effects of silicone.

Quaternary ammonium salts or tertiary amines have also been incorporated into hair detergents (shampoos) in order to produce conditioning effects on hair after shampoo.

However, a combined use of a quaternary ammonium salt or a tertiary amine with an anionic surface active agent not only causes reduction in foaming properties but fails to produce sufficient conditioning effects. Therefore, other conditioning components have been used in combination.

It has therefore been demanded to develop a detergent composition which is low-irritant to the skin and exhibits high foaming properties and high conditioning effects.

SUMMARY OF THE INVENTION

In the light of the above-mentioned circumstances, the inventors have conducted extensive study on detergents containing an amidoether carboxylic acid and found, as a result, that an amidoether carboxylic acid containing a large quantity of polyoxyethylene glyceryl ether or polyoxyethylene glyceryl ether carboxylic acid which are impurities originated in the starting material or a pure amidoether carboxylic acid per se is inferior in foaming properties. As a result of further investigations, it was found that an amidoether derivative mixture containing an amidoether at a specific ratio with a content of glycerin derivatives being controlled within a given ratio provides a detergent which hardly irritates the skin, exhibits excellent foaming properties, produces creamy foam, feels excellent to the touch during washing, and also has conditioning effects such as smooth touch of hair or the skin after washing. The present invention has been completed based on this finding.

Thus, the present invention provides a detergent composition comprising components (A) and (B):

(A) an amidoether derivative mixture (A) comprising an amidoether carboxylic acid or a salt thereof represented by formula (1), an amidoether represented by formula (2), and a glycerin derivative represented by formula (3); and (B) a conditioning component

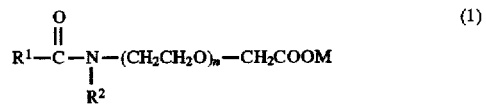

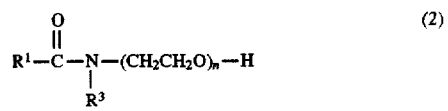

$$\begin{array}{c} \text{CH}_2\text{OR}^4 \\ | \\ \text{CHOR}^4 \\ | \\ \text{CH}_2\text{OR}^4 \end{array} \quad (3)$$

wherein $R^1$ represents a straight-chain or branched alkyl or alkenyl group having 5 to 23 carbon atoms or a phenyl group substituted with the alkyl group;

$R^2$ represents a hydrogen atom, $-(CH_2CH_2O)_n CH_2COOM$, $-(CH_2CH_2O)_m H$ or an alkyl group having 1 to 3 carbon atoms;

M represents a hydrogen atom, an alkali metal, an alkaline earth metal, an ammonium group, an alkanolamine or a basic amino acid;

n and m, which may be the same or different, each represent a number of from 1 to 20;

$R^3$ represents a hydrogen atom, $-(CH_2CH_2O)_m H$ or an alkyl group having 1 to 3 carbon atoms; and $R^4$ represents a hydrogen atom, $-(CH_2CH_2O)_n CH_2COOM$ or $-(CH_2CH_2O)_m H$;

in which $R^1$, M, n, and m in formulae (1), (2) and (3) may be the same or different;

wherein the total amount of the amidoether carboxylic acid or a salt thereof (1) and the amidoether (2) is 50% by weight or more based on the solid content of the amidoether derivative mixture (A);

the weight ratio of the amidoether carboxylic acid or a salt thereof (1) to the amidoether (2) is from 99:1 to 10:90; and the amount of the glycerin derivative (3) is 5% by weight or less based on the solid content of the amidoether derivative mixture (A).

The detergent composition according to the present invention hardly irritates the skin, exhibits excellent foaming properties, produces creamy foam, feels excellent to the touch during washing, and also has conditioning effects such as smooth touch of hair or the skin after washing.

Further, the detergent composition of the present invention, when applied to hair, gives a gloss to hair and makes a comb run smoothly after shampoo and, when applied to the skin, gives the skin smooth touch after washing.

DETAILED DESCRIPTION OF THE INVENTION

In the amidoether derivative mixture (A) which can be used in the present invention, $R^1$ in formula (1) or (2) preferably represents an alkyl or alkenyl group having 7 to 17 carbon atoms or a phenyl group substituted with the alkyl group, such as a heptyl group, a nonyl group, an undecyl group, a tridecyl group, a pentadecyl group, a heptadecyl group, and a heptadecenyl group, with an undecyl group and a tridecyl group being especially preferred. $R^2$ and $R^3$ each preferably represent a hydrogen atom or an alkyl group having 1 to 3 carbon atoms. n and m each preferably represent a number of from 1 to 15, more preferably of from 1 to 10, and most preferably of from 2 to 7. Examples of M include sodium, potassium, magnesium, calcium, monoethanolamine, diethanolamine, triethanolamine, arginine and lysine. Preferred among them are sodium, potassium, magnesium and calcium. In view of improved touch of hair on rinsing and after drying, magnesium is particularly preferred. Especially, when a cation polymer is used as the conditioning component (B), magnesium is preferred.

Preferred examples of the amidoether carboxylic acid or a salt thereof represented by formula (1) (hereinafter referred to as amidoether carboxylic acid or a salt thereof (1)) in the amidoether derivative mixture (A) include various compounds represented by formula (1). Particularly preferred examples include lauric monoethanolamide polyoxyethylene ether acetic acid (n=1 to 10), myristic monoethanolamide polyoxyethylene ether acetic acid (n=1 to 10), palmitic monoethanolamide polyoxyethylene ether acetic acid (n=1 to 10), stearic monoethanolamide polyoxyethylene ether acetic acid (n=1 to 10), and salts thereof, with lauric monoethanolamide polyoxyethylene ether acetic acid (n=2 to 7) and myristic monoethanolamide polyoxyethylene ether acetic acid (n=2 to 7) being most preferred.

Preferred examples of the amidoether represented by formula (2) (hereinafter referred to as amidoether (2)) in the amidoether derivative mixture (A) include various compounds represented by formula (2). Particularly preferred examples include lauric monoethanolamide polyoxyethylene ether (n=1 to 10), myristic monoethanolamide polyoxyethylene ether (n=1 to 10), palmitic monoethanolamide polyoxyethylene ether (n=1 to 10), and stearic monoethanolamide polyoxyethylene ether (n=1 to 10), with lauric monoethanolamide polyoxyethylene ether (n=2 to 7) and myristic monoethanolamide polyoxyethylene ether (n=2 to 7) being most preferred.

The total amount of the amidoether carboxylic acid or a salt thereof (1) and the amidoether (2) in the amidoether derivative mixture (A) is preferably 50% or more, more preferably 60% or more, still preferably 70% or more, most preferably 80% or more, by weight based on the solids content of the amidoether derivative mixture (A).

The weight ratio of the amidoether carboxylic acid or a salt thereof (1) to the amidoether (2) is preferably from 99:1 to 10:90, more preferably from 95:5 to 60:40, still preferably from 92:8 to 70:30.

The amount of the glycerin derivative (3) in the amidoether derivative mixture (A) is preferably 5% by weight or less (i.e., 0 to 5% by weight), more preferably 3% by weight or less (i.e., 0 to 3% by weight) based on the solids content of the amidoether derivative mixture (A), and it is most preferred that component (A) contains substantially no glycerin derivative (3). If the amount of the glycerin derivative (3) exceeds 5% by weight based on the solids content, the foaming properties of the mixture tend to be reduced. With regards to inorganic salts, e.g., sodium chloride, which are impurities other than the glycerin derivative (3) in component (A), the smaller the content, the better.

The process for preparing the amidoether derivative mixture (A) is not particularly restricted. For example, the amidoether carboxylic acid may be directly prepared by reacting a part of the amidoether to obtain amidoether carboxylic acid. Alternatively, it may be prepared by externally adding the amidoether to the amidoether carboxylic acid. Illustrative processes for preparing the amidoether derivative mixture include a process in which a fatty acid alkanolamide is prepared by starting with a fatty acid lower alcohol ester, such as a fatty acid methyl ester; a process in which an alkanolamide is prepared by starting with fats and oils; and a process in which an alkanolamide is prepared by starting with a fatty acid. Of these processes, the process starting with a fatty acid lower alcohol ester, such as a fatty acid methyl ester, is preferred; for the resulting reaction mixture is less colored and contains substantially no glycerin derivatives as impurities. Where the other processes are carried out, for example, fat and oil having a coconut oil fatty acid composition as a starting material is directly converted into an alkanolamide, and the resulting alkanolamide is alkoxylated and then carboxylmethylated, glycerin derivatives originating in the fat and oil are unfavorably produced in a considerable amount, resulting in low yields of compounds (1) and (2). The ratio of the amidoether carboxylic acid (1) to the amidoether (2) in the amidoether derivative mixture (A) can be adjusted by suitably selecting the reaction conditions, such as the molar ratio of monohalogenoacetic acid or a salt thereof (e.g., monohalogenoacetic acid alkali salt) to the amidoether (2), the manner of mixing.

The amidoether carboxylic acids (1) and the amidoethers (2) in the amidoether derivative mixture (A) may be used either individually or as a combination of two or more thereof.

The detergent composition of the present invention further comprises a conditioning component (B) in addition to the amidoether derivative mixture (A).

Examples of the conditioning component (B) include a cationic polymer, a silicone, a silicone derivative, a quaternary ammonium salt, a tertiary amine, and oils such as higher alcohols, lanolin, squalene, hydrocarbons and protein derivatives. The conditioning component (B) may be used either individually or as a combination of two or more thereof.

The conditioning component (B) to be used in the present invention is preferably at least one member selected from the group consisting of a cationic polymer, a silicone, a silicone derivative, a quaternary ammonium salt, and a tertiary amine. These preferred conditioning components will be described below more specifically.

The cationic polymers which can be used in the present invention as the conditioning component (B) include, for example, cationic cellulose derivatives, cationic starch, cationic gum guaiac derivatives, diallyl quaternary ammonium homopolymers, (diallyl quaternary ammonium salt/acrylamide) copolymers, (diallyl quaternary ammonium salt/acrylic acid) copolymers, (diallyl quaternary ammonium/acrylic acid/acrylamide) terpolymers, quaternarized polyvinylpyrrolidone derivatives, and polyglycol polyamine condensates. Preferred examples include cationic cellulose derivatives, diallyl quaternary ammonium homopolymers, and (diallyl quaternary ammonium salt/acrylamide and/or acrylic acid) copolymers.

The cationic cellulose derivatives preferably include those represented by formula (4):

wherein A represents a residue of an anhydroglucose unit; a represents an integer of 50 to 20,000; and $R^5$ independently represents a substituent represented by formula (5):

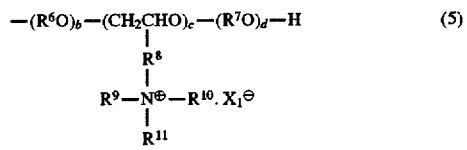

wherein $R^6$ and independently represent an alkylene group having 2 or 3 carbon atoms; b and d indepenently represent an integer of 0 to 10; c represents an integer of 0 to 3; $R^8$ represents an alkylene or hydroxyalkylene group having 1 to 3 carbon atoms; $R^9$, $R^{10}$, and $R^{11}$ independently represent an alkyl group having 1 to 18 carbon atoms, an aryl group or an aralkyl group, or they may form a heterocyclic ring together with the adjacent nitrogen atom; and $X_1^-$ represents an anion, such as a chloride ion, a bromide ion, an iodide ion, a sulfate ion, a sulfonate ion, a methylsulfate ion, a phosphate ion, and a nitrate ion.

The degree of cation substitution of the cationic cellulose derivative is preferably 0.01 to 1, that is, the value c per anhydroglucose unit is preferably 0.01 to 1, still preferably 0.02 to 0.5, on an average. The sum of b and d is preferably 1 to 3 on an average. If the degree of cation substitution is less than 0.01, sufficient effects cannot be obtained. On the other hand, it may exceed 1, but in this case the reaction yield is reduced. The cationic cellulose derivative preferably has a molecular weight of 100,000 to 3,000,000.

The cationic starch preferably includes those represented by formula (6):

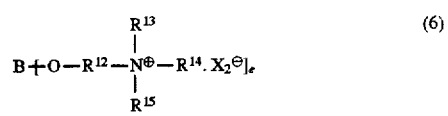

wherein B represents a starch residue; $R^{12}$ represents an alkylene group or a hydroxyalkylene group; $R^{13}$, $R^{14}$, and R15 independently represent an alkyl group having 1 to 10 carbon atoms, an aryl group or an aralkyl group, or they may form a heterocyclic ring together with the adjacent nitrogen atom; $X_2^-$ represents an anion, such as a chloride ion, a bromide ion, an iodide ion, a sulfate ion, a sulfonate ion, a methylsulfate ion, a phosphate ion, and a nitrate ion; and e represents a positive integer.

The degree of cation substitution of the cationic starch is preferably 0.01 to 1, that is, the cationic starch preferably has 0.01 to 1, still preferably 0.02 to 0.5, cationic group per anhydroglucose unit. If the degree of cation substitution is less than 0.01, sufficient effects cannot be obtained. On the other hand, it may exceed 1, but in this case the reaction yield is reduced.

The cationic gum guaiac derivatives preferably include those represented by formula (7):

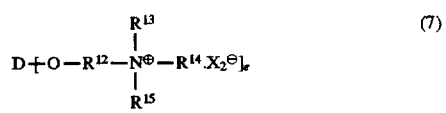

wherein D represents a gum guaiac residue; and $R^{12}$ $R^{13}$, $R^{14}$, $R^{15}$, $X_2^-$, and e are as defined above.

The degree of cation substitution of the cationic gum guaiac derivative is preferably 0.01 to 1, that is, the cationic gum guaiac preferably has 0.01 to 1, still preferably 0.02 to 0.5, cationic group per sugar unit.

Cationic polymers of this type are described in Japanese Patent Publications 58-35640 and 60-46158 also U.S. Pat. No. 4,298,494 and U.S. Pat. No. 5,037,818 and Japanese Patent Application Laid-Open 58-53996 also U.S. Pat. No. 4,364,837 which are incorporated herein by reference, and are also commercially sold by Celanese-Stein Hall under a series of trade names of "Jaguar".

The (diallyl quaternary ammonium salt/acrylamide) copolymers preferably include those represented by formulae (8) and (9):

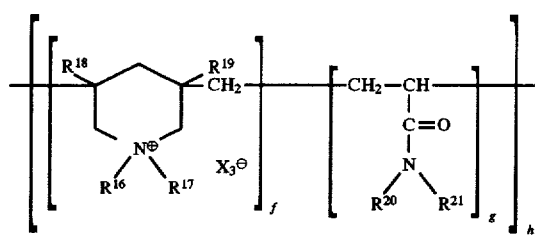
(8)

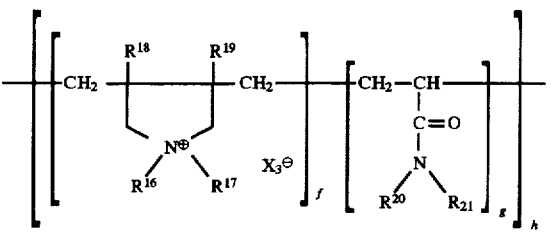
(9)

wherein $R^{16}$ and $R^{17}$ independently represent a hydrogen atom, an alkyl group having 1 to 18 carbon atoms, a phenyl group, an aryl group, a hydroxyalkyl group, an amidoalkyl group, a cyanoalkyl group, an alkoxyalkyl group or a carboalkoxyalkyl group; $R^{18}$, $R^{19}$, $R^{20}$ and $R^{21}$ independently represent a hydrogen atom, a lower alkyl group (for example, 1 to 3 carbon atoms) or a phenyl group; $X_3^-$ represents an anion, such as a chloride ion, a bromide ion, an iodide ion, a sulfate ion, a sulfonate ion, a methylsulfate ion, and a nitrate ion; f and g independently represent an integer of 1 to 50; and h represents an integer of 150 to 8,000.

The (diallyl quaternary ammonium salt/acrylamide) copolymers preferably have a molecular weight of about 30,000 to 2,000,000, still preferably 100,000 to 1,000,000.

The (diallyl quaternary ammonium salt/acrylic acid) copolymers preferably include those represented by formulae (10) and (11):

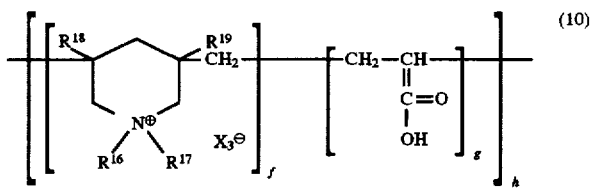
(10)

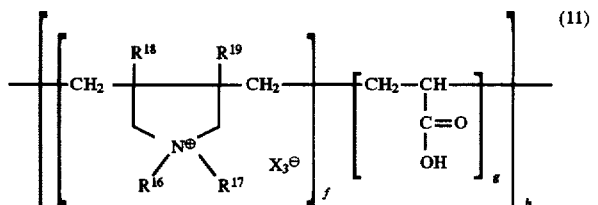
(11)

wherein $R^{17}$, $R^{18}$, $R^{19}$, $X_3^-$, f, g, and h are as defined above.

The quaternarized polyvinylpyrrolidone derivatives preferably include those represented by formula (12):

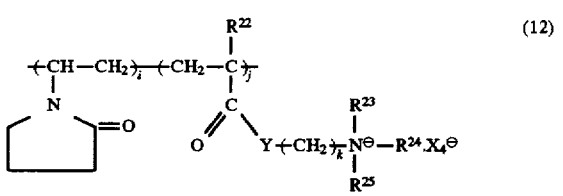
(12)

wherein $R^{22}$ represents a hydrogen atom or an alkyl group having 1 to 3 carbon atoms; $R^{23}$, $R^{24}$, and $R^{25}$ independently represent a hydrogen atom, an alkyl group having 1 to 4 carbon atoms, a hydroxyalkyl group, an amidoalkyl group, a cyanoalkyl group, an alkoxyalkyl group or a carboalkoxyalkyl group; Y represents an oxygen atom or —NH—; $X_4^-$ represents an anion, such as a chloride ion, a bromide ion, an iodide ion, a sulfate ion, a sulfonate ion, an alkylsulfate ion having 1 to 4 carbon atoms, a phosphate ion, or a nitrate ion; i and j independently represent an integer, with the sum of i +j being from 20 to 8000; and k represents an integer of from 1 to 10.

The quaternarized polyvinylpyrrolidone derivatives preferably have a molecular weight of 10,000 to 2,000,000, still preferably 50,000 to 1,500,000. The cationic nitrogen content originated in a cationic polymer which is contained in the quaternarized polyvinylpyrrolidone derivative is preferably 0.004 to 0.2%, still preferably 0.01 to 0.15%, based on the vinyl polymer. If it is less than 0.004%, sufficient effects cannot be produced. The cationic nitrogen content exceeding 0.2%, though favorable for performance properties, causes coloration and is economically disadvantageous.

The polyglycol polyamine condensates preferably include those represented by formula (13):

(13)

wherein $R^{26}$, $R^{28}$, $R^{29}$, and $R^{31}$ independently represent a hydroxyalkylene group having 2 to 4 carbon atoms; $R^{27}$ and $R^{30}$ independently represent an alkylene group having 2 or 3 carbon atoms; $R^{32}$ represents a straight-chain or branched alkyl group having 6 to 20 carbon atoms; l and r independently represent an integer of from 10 to 20; p represents an integer of from 2 to 6; q represents an integer of from 2 to 4; and s represents an integer of from 1 to 50.

In addition to the above-described cationic polymers, an (adipic acid/dimethylaminohydroxypropyl-ethylenetriamine) copolymer ("Cultalethene" produced by Sandoz Ltd., U.S.A.) and all the cationic polymers disclosed in Japanese Patent Application Laid-Open 53-139734 and 60-60-36407, which are incorporated herein by reference, can also be used.

These cationic polymers may be used as the conditioning component (B) either individually or as a combination of two or more thereof.

The silicones or silicone derivatives which can be used as the conditioning component (B) will be described below.

The silicones or silicone derivatives as the conditioning component (B) are not particularly limited and include i) to ix) shown below.

i) Dimethylpolysiloxane

Included are those represented by formula (14):

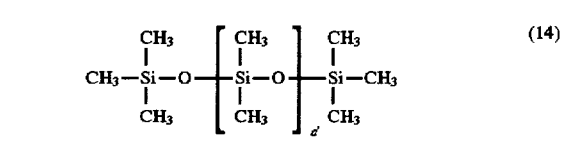
(14)

wherein a' represent a number of from 3 to 20,000.

ii) Methylphenylpolysiloxane

Included are those represented by formulae (15a) and (15b):

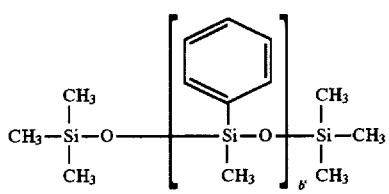
(15a)

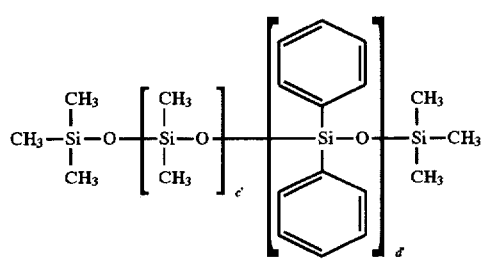
(15b)

wherein b' represents a number of from 1 to 20,000; and c' and d' independently represent a number, with the sum of c'+d' being from 1 to 500.

iii) Polyether-Modified Silicone

Included are those represented by formulae (16a), (16b) and (16c):

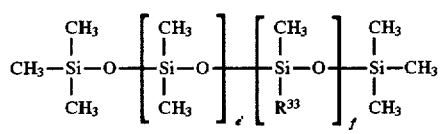
(16a)

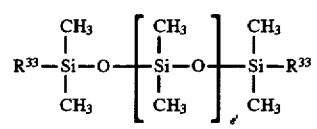
(16b)

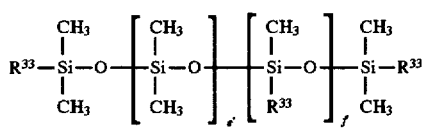
(16c)

wherein $R^{33}$ represents —$(CH_2)_3$—O—$(C_2H_4O)_{g'}$—$(C_3H_6O)_{h'}$—E, wherein E represents a hydrogen atom or an alkyl group having 1 to 12 carbon atoms; and g' and h' independently represent an integer of from 0 to 50, with the sum of g'+h' being at least 1; e' represents an integer of from 1 to 2,000; and f' represents an integer of from 1 to 1,000.

iv) Epoxy-Modified Silicone

Included are those represented by formula (17):

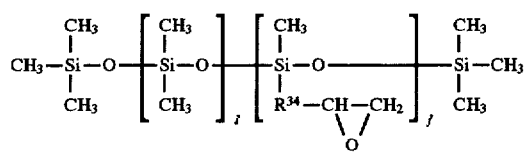
(17)

wherein $R^{34}$ represents an alkylene group having 1 to 3 carbon atoms; i' represents a number of from 1 to 500, preferably from 1 to 250; and j' represents a number of from 1 to 50, preferably 1 to 30.

v) Fluorine-Modified Silicone

Included are those represented by formula (18):

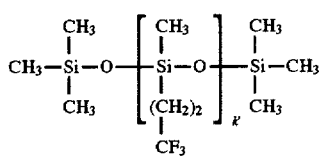
(18)

wherein k' represents a number of from 1 to 400, preferably 1 to 250.

vi) Alcohol-Modified Silicone

Included are those represented by formulae (19a) and (19b):

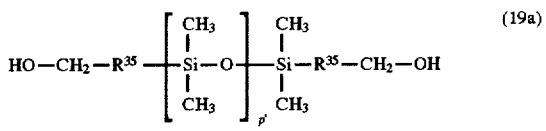
(19a)

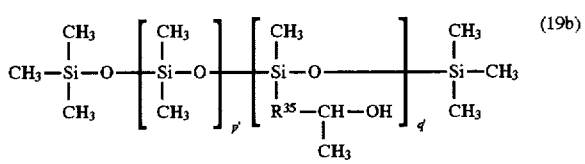
(19b)

wherein R35 represents a single bond (direct linkage) or an alkylene group having 1 to 4 carbon atoms; and p' and q' independently represent a number of from 1 to 500, preferably 1 to 200.

vii) Alkyl-Modified Silicone

Included are those represented by formulae (20a) and (20b):

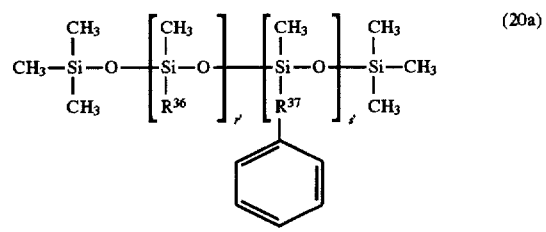
(20a)

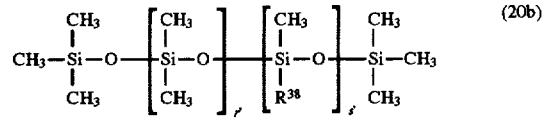
(20b)

wherein $R^{36}$ represents an alkyl group having 2 to 18 carbon atoms; $R^{37}$ represents a single bond (direct linkage) or an alkylene group having 1 to 4 carbon atoms; $R^{38}$ represents an alkyl group having 10 to 16 carbon atoms; and r' and s' independently represent a number of from 1 to 500, preferably 1 to 200.

viii) Alkoxy-Modified Silicone

Included are those represented by formula (21):

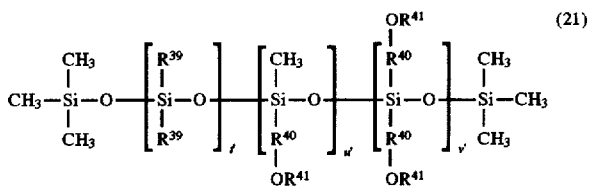
(21)

wherein $R^{39}$ represents a methyl group or a phenyl group; $R^{40}$ represents a single bond (direct linkage) or an alkylene group having 1 to 6 carbon atoms; $R^{41}$ represents an alkyl group having 1 to 28 carbon atoms, preferably 12 to 22 carbon atoms; t' represents an integer of from 1 to 3,000; and u' and v' independently represent a number, with the sum of u'+v' being from 1 to 500.

ix) Amino-Modified Silicone

Included are those represented by formulae (22a) and (22b):

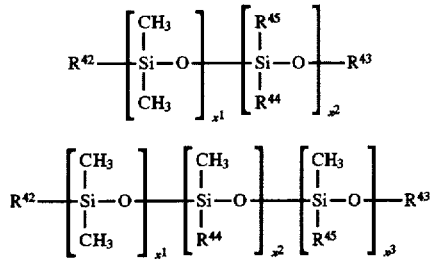

wherein $R^{42}$ represents a methyl group or a hydroxyl group; $R^{43}$ represents a hydrogen atom or a methyl group; $R^{44}$ represents an aminoalkyl group represented by formulae:

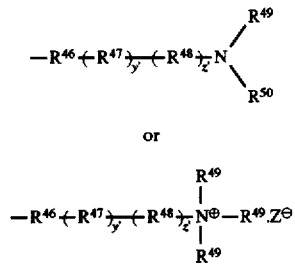

or

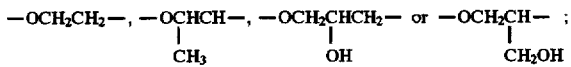

wherein $R^{46}$ represents a divalent hydrocarbon group; $R^{47}$ represents a single bond (direct linkage),

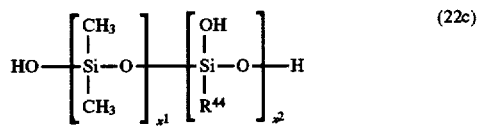

$R^{48}$ represents a single bond (direct linkage) or —NHCH$_2$CH$_2$—; $R^{49}$ and $R^{50}$ independently represent a hydrogen atom or a monovalent hydrocarbon group; y' and z' independently represent an integer of from 1 to 6; and Z represents a halide ion or an organic anion;

$R^{45}$ represents a hydroxyl group, a hydroxyalkyl group or a polyoxyalkylene group with a hydrogen atom bonded at the terminal oxygen atom; and $x^1$, $x^2$, and $x^3$ independently represent an integer dependent on the molecular weight.

Particularly preferred amino-modified silicones are those represented by formula (22c):

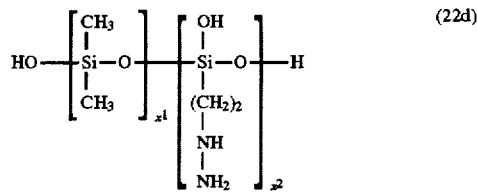

wherein $R^{44}$, $x^1$, and $x^2$ are as defined above.

The amino-modified silicones of formula (22c) typically include those represented by formula (22d) shown below which have an average molecular weight of 3,000 to 100,000 and are described in Cosmetic Ingredient Dictionary (3rd Ed.) under the name of "Amodimethicone".

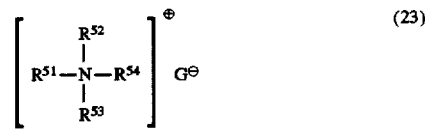

wherein $x^1$ and $x^2$ are as defined above.

These amino-modified silicones are preferably used in the form of an aqueous emulsion, which can be prepared, for example, by the method described in Japanese Patent Publication 56-38609 which is incorporated herein by reference, in which a cyclic di-di-organo-polysiloxane and an organo-di-alkoxy silane having an aminoalkyl group and a hydroxyl group, a hydroxyalkyl group, an oxyalkylene group or a polyoxyalkylene group are emulsion-polymerized in the presence of a quaternary ammonium salt type surfactant and water. The content of the amino-modified silicone in the resulting aqueous emulsion usually ranges from 20 to 60% by weight, preferably 30 to 50% by weight.

Examples of preferred commercially available products of the amino-modified silicone aqueous emulsions include SM 8702C (produced by Toray Silicone Co., Ltd.) and DC 929 (produced by Dow Corning Corp.).

The aqueous emulsion of the silicone or silicone derivative may be prepared upon use by making the silicone or silicone derivative which is not in the form of an aqueous emulsion into an aqueous emulsion by using water and a surfactant.

Among the aforementioned silicones and silicone derivatives, particularly preferred as the conditioning component (B) are dimethylpolysiloxane, methylphenylpolysiloxane, polyether-modified silicone, and amino-modified silicone. The silicones and silicone derivatives may be used either individually or as a combination of two or more thereof as the conditioning component (B).

The quaternary ammonium salts which can be used as the conditioning component (B) in the present invention will be described below.

The quaternary ammonium salts as the conditioning component (B) are not particularly limited and include those represented by formulae (23) and (24):

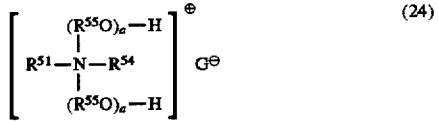

wherein at least one of $R^{51}$, $R^{52}$, $R^{53}$, and $R^{54}$ represents an alkyl or alkenyl group which may be substituted with an alkoxy group, an alkenyloxy group, an alkanoylamino group, an alkylalkanoylamino group, a hydroxyalkylalkanoylamino group, an alkenoylamino group, an alkylalkenoylamino group or a hydroxyalkylalkenoylamino group, the substituted or unsubstituted alkyl or alkenoyl group having 8 to 28 carbon atoms in total; and the rest of them independently represent a benzyl group or an alkyl or hydroxyalkyl group having 1 to 5 carbon atoms; $R^{55}$ represents an alkylene group having 2 or 3 carbon atoms; G represents a halide ion or an organic anion; and a" represents an integer of from 1 to 20.

The quaternary ammonium salts represented by formula (23) are preferred. Of the quaternary ammonium salts of formula (23), preferred are those represented by formulae (23a) through (23c):

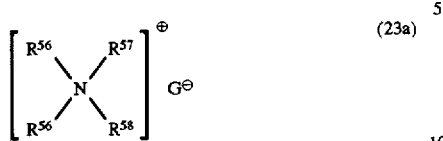 (23a)

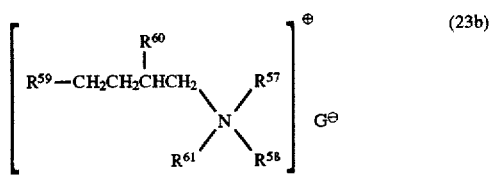 (23b)

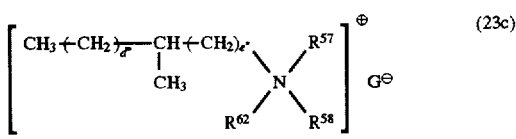 (23c)

wherein $R^{56}$ represents a mixed alkyl group composed of (a) a branched alkyl group represented by formula

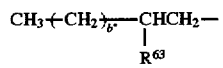

(wherein $R^{63}$ represents a methyl group or an ethyl group; and b" represents an integer for making the total carbon atom number in the alkyl group 8 to 16) and (b) a straight-chain alkyl group represented by formula $CH_3-(CH_2)_{c'}$ (wherein c' represents an integer of from 7 to 15), the mixed alkyl group having a branching ratio, (a)/[(a)+(b)], of 10 to 100%; $R^{57}$ and $R^{58}$ independently represent a benzyl group, or an alkyl or hydroxyalkyl group having 1 to 3 carbon atoms; $R^{59}$ and $R^{60}$ independently represent an alkyl group having 2 to 12 carbon atoms; $R^{61}$ represents

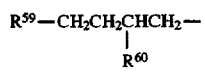

or an alkyl group having 1 to 3 carbon atoms; $R^{62}$ represents

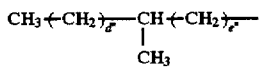

or an alkyl group having 1 to 3 carbon atoms; d" represents an integer of from 2 to 14; e" represents a number of from 3 to 11, with the sum of d" and e" being 9 to 21; and G represents a halide ion or an organic anion.

The branched quaternary ammonium salts of formula (23a) are synthesized, for example, from oxo alcohols having 8 to 16 carbon atoms. Examples of the branched quaternary ammonium salts include compounds having an alkyl moiety derive from the oxo alcohol, such as dialkyldimethylammonium salts, dialkylmethylhydroxyethylammonium salts, and dialkylmethylbenzylammonium salts.

In the present invention, the branched quaternary ammonium salts of formula (23a) in which $R^{56}$ has a branching ratio of 10 to 100% are usually employed, with those in which the branching ratio of $R^{56}$ is 10 to 50% being preferred. The total carbon atom number in $R^{56}$ is usually 8 to 16. The branched quaternary ammonium salts of formula (23a) in which $R^{56}$ has a given distribution of the carbon atom number are preferred. In particular, those in which $R^{56}$ has the following carbon atom number distribution are preferred.

$C_8$ to $C_{11}$: 5% or less
$C_{12}$: 10 to 35%
$C_{13}$: 15 to 40%
$C_{14}$: 20 to 45%
$C_{15}$: 5 to 30%
$C_{16}$: 5% or less Examples of such branched quaternary ammonium salts include dialkyldimethylammonium chlorides in which each of the alkyl moieties has 8 to 16 carbon atoms and a branching ratio of 10 to 50%.

The branched quaternary ammonium salts of formula (23b) are usually synthesized from a Guerbet alcohol having 8 to 28 carbon atoms represented by formula below:

wherein $R^{59}$ and $R^{60}$ are as defined above.

Examples of suitable branched quaternary ammonium salts of formula (23b) include alkyltrimethylammonium salts, alkyldimethylbenzyl-ammonium salts, dialkyldimethylammonium salts, dialkylethylammonium salts, dialkylmethylhydroxyethylammonium salts, and dialkylmethylbenzylammonium salts, in which the alkyl moiety or moieties is/are those derived the Guerbet alcohol. Particularly preferred of them are 2 decyltetradecyl-trimethylammonium chloride, 2-dodecylhexadecyl-trimethylammonium chloride, di-2-hexyldecyl-dimethylammonium chloride, and di-2-octyldodecyl-dimethylammonium chloride.

The methyl-branched quaternary ammonium salts represented by formula (23c) preferably include those in which the sum of d" and e" is 15.

In the quaternary ammonium salts of formulae (23), (24), (23a), (23b), and (23c), the anion component represented by G includes a halide ion, such as chloride ion, an iodide ion and a bromide ion; and an organic anion, such as a methylsulfate ion, an ethylsulfate ion, a methylphosphate ion and an ethylphosphate ion.

The above-described quaternary ammonium salts may be used as the conditioning component (B) either individually or as a combination of two or more thereof.

The tertiary amines which can be used as the conditioning component (B) in the present invention will be described below.

The tertiary amines to be used as the conditioning component (B) are not particularly limited and include those represented by formulae (25) and (26):

 (25)

 (26)

wherein $R^{51}$, $R^{52}$, $R^{53}$, $R^{55}$, and a" are as defined above.

Of the above-mentioned tertiary amines preferred are amidoamines represented by formula (25a):

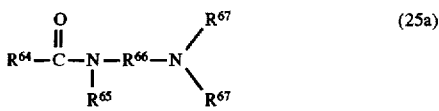

(25a)

wherein $R^{64}$ represents a straight-chain or branched alkyl or alkenyl group having 6 to 26 carbon atoms; $R^{65}$ represents a hydrogen atom or an alkyl or hydroxyalkyl group having 1 to 4 carbon atoms; $R^{66}$ represents an alkylene group having 1 to 4 carbon atoms; and $R^{67}$ represents an alkyl or hydroxyalkyl group having 1 to 4 carbon atoms.

Examples of suitable tertiary amines (25a) are palmitic dimethylaminoethylamide, palmitic diethylaminoethylamide, palmitic dipropylaminoethylamide, palmitic dimethylaminopropylamide, palmitic diethylaminopropylamide, palmitic dipropylaminopropylamide, stearic dimethylaminoethylamide, stearic diethylaminoethylamide, stearic dipropylaminoethylamide, stearic dimethylaminopropylamide, stearic diethylaminopropylamide, stearic dipropylaminopropylamide, palmitic dimethylaminoethylmethylamide, palmitic dimethylaminopropylmethylamide, palmitic dimethylaminoethylhydroxyethylamide, and palmitic dimethylaminopropylhydroxyethylamide.

These tertiary amines may be used as the conditioning component (B) either individually or as a combination of two or more thereof.

While the amount of component (A) in the detergent composition of the present invention is not particularly limited, it is preferably 5 to 50%, still preferably 6 to 30%, and most preferably 7 to 25%, by weight, based on the total amount of the detergent composition, from the standpoint of foaming properties.

In the conditioning component (B), the amount of the conditioning component (B) in the detergent composition is preferably 0.01 to 10% by weight, based on the total amount of the detergent composition, while not limited.

More specifically, where the above-described cationic polymer is used as the conditioning component (B), a preferred amount is 0.01 to 5%, particularly 0.05 to 1.5%, by weight. Where the above-described silicone or silicone derivative is used as the conditioning component (B), a preferred amount is 0.05 to 10%, still preferably 0.1 to 5%, and most preferably 0.2 to 3%, by weight. In using the above-described quaternary ammonium salt or tertiary amine as the conditioning component (B), a preferred amount is 0.05 to 10%, still preferably 0.1 to 5%, and most preferably 0.2 to 4%, by weight.

It is preferable that the detergent composition of the present invention be adjusted to a pH of preferably 2 to 10, more preferably 4 to 8, still preferably 4 to 7, as measured as an aqueous solution containing 5% by weight of the active components, with a known acidic or alkaline chemical commonly used in conventional detergent compositions.

In addition to the amidoether derivative mixture (A) and the conditioning component (B), the detergent composition may further contain conditioning components other than the above-mentioned conditioning component (B). Where the other conditioning components are formulated, the conditioning components can be used in an amount of from 0.1 to 5% by weight based on the detergent composition of the present invention.

In addition to the above-mentioned essential components, surface active agents other than amidoether carboxylic acid, such as anionic surface agents or nonionic surface active agents, for example, alkyl polyglycosides can be added to the detergent composition of the present invention so far as the effects of the present invention are not impaired.

The detergent composition may furthermore contain components conventionally used in detergent compositions as far as the effects of the present invention are not impaired. Such optional components include water-soluble polymers such as methyl cellulose, hydroxyethyl cellulose, carboxyvinyl polymer, and polysaccharides (e.g., xantham gum); viscosity modifiers such as polyoxyalkylene sorbitan esters, polyoxyethylene glycol distearate, and ethanol; chelating agents such as ethylenediaminetetraacetic acid (EDTA) and phosphoric acid salts; antiseptics such as methyl p-hydroxybenzoate and butyl p-hydroxybenzoate; nutrient components such as vitamins or precursors thereof; animal or vegetable extracts such as lecithin, or derivatives thereof; fine particles of polymers such as nylon and polyethylene; antiinflammatory agents such as potassium glycyrrhizinate; bactericidal agents or antidandruff agents such as Triclosan, Triclocarban, Octopirox, and Zinc Pyrithione; antioxidants such as dibutylhydroxytoluene; pearly luster imparting agents, ultraviolet absorbers, pH adjusting agents, dyes, perfumes.

The detergent composition of the present invention is applicable as not only a detergent for hair or the skin but a detergent for various purposes, such as detergents for dishes or clothing, bath foam, and the like. Also, it is preferable that the total amount of all surface active agents inclusive of the amidoether derivative mixture (A) in the detergent composition is at least 30% by weight in the case of a solid preparation, at least 20% by weight in the case of a paste preparation, or at least 10% by weight in the case of a liquid preparation.

The present invention will now be illustrated in greater detail with reference to Examples, but it should be understood that the present invention is not deemed to be limited thereto. Examples 1 to 6 illustrate synthesis of amidoether carboxylic acid salts containing amidoether, and Comparative Examples 1 to 3 are comparative examples corresponding to Examples 1 to 6. Unless otherwise indicated, all the percents are given by weight.

EXAMPLE 1

Synthesis of Amidoether Carboxylic Acid Salt Containing Amidoether:

A mixture of 214.4 g (1 mol) of methyl laurate, 61.7 g (1.02 mol) of monoethanolamine, and 15.3 g of a 30% methanol solution of sodium methoxide was heated at 90° C. and 50 mmHg for 5 hours. To the resulting product was added 88.2 g (2 mol) of ethylene oxide at 100 to 110° C. and a gauge pressure of 0 to 3.5 atm.

The resulting reaction mixture weighing 331 g was heated to 70 to 75° C., and 174.8 g (1.5 mol) of sodium monochloroacetate (hereinafter abbreviated as SMCA) and 65.2 g of solid sodium hydroxide were each added thereto over a period of 4 hours. SMCA and sodium hydroxide were each divided into 5 equal portions, and each portion was added at the start of the reaction and after 1, 2, 3 and 4 hours from the start of the reaction. After the final addition, the reaction mixture was aged for 1 hour. Then, the reaction temperature was raised to 85° C., and 5.3 g of water was added thereto, followed by further aging for 1 hour to obtain 592 g of a carboxylmethylized reaction mixture. To the reaction mixture was added 500 g of water, and the mixture was adjusted to pH 2.8 by addition of a 36% aqueous solution of hydrochloric acid at 90° C., followed by stirring for 1 hour. The reaction mixture was allowed to stand for 1 hour for phase separation to obtain 545 g of a product of an acid form. The resulting acid form product was adjusted to pH 7 with a 30% aqueous sodium hydroxide solution, and water was added thereto till the solution became clear thereby to obtain amidoether derivative mixture 2 shown in Table 1 below.

EXAMPLES 2 TO 6

Synthesis of Amidoether Carboxylic Acid Salts Containing Amidoether:

The amidoether derivative mixtures 1, 3, 5, and 6 shown in Table 1 were obtained in the same manner as in Example 1. The molar ratios of the sodium monochroloacetic acid to the amidoether were determined to 1.7, 1.5, 1.5 and 1.4, respectively, and the molar ratios of the solid sodium hydroxide to the amidoether were determined to 1.85, 1.63, 1.63 and 1.52, respectively. Further, the amidoether derivative mixture 4 shown in Table 1 was prepared in the same manner as in Example 1 except that the conversion to an acid form and purification were not conducted and the reaction mixture was merely adjusted to pH 7 with a 30% aqueous sodium hydroxide solution.

EXAMPLE 7

Synthesis of Magnesium Salt of Amidoether Carboxylic Acid Containing Amidoether:

The acid form product obtained in Example 1 was neutralized to a pH of 6 to 7 with an aqueous dispersion of a 30% magnesium hydroxide, and water was added thereto until the solution became clear thereby to obtain the amidoether derivative mixture 7 shown in Table 1.

COMPARATIVE EXAMPLE 1

Synthesis of Amidoether Carboxylic Acid Salt Containing Glycerin Derivative:

Purified coconut oil weighing 510.6 g (2.2 mol) was dissolved at 35° C. The mixture of the coconut oil solution, 138.8 g (2.3 mol) of monoethanolamine, and 5.1 g of a 30% methanol solution of sodium methoxide was heated at 70° C. for 2 hours and then at 105° C. for 6 hours. To the resulting product was introduced 298 g (6.75 mol) of ethylene oxide at 100 to 110° C. under a gauge pressure of 0 to 3.5 atm over a period of 30 minutes.

The resulting reaction mixture (675 g) was heated to 70 to 75° C., and 281.7 g (2.41 mol) of SMCA and 105.1 g of solid sodium hydroxide were each added thereto over a period of 4 hours. SMCA and sodium hydroxide were each divided into 5 equal portions, and each portion was added at the start of the reaction and after 1, 2, 3 and 4 hours from the start of the reaction. After the final addition, the reaction mixture was aged for 1 hour. Then, the reaction temperature was raised to 85° C., and 5 g of water was added thereto, followed by further aging for 1 hour to obtain 1039 g of a reaction mixture. To the reaction mixture was added 500 g of water, and the mixture was adjusted to pH 7 by addition of a 36% aqueous HCl solution at 50° C. and diluted with water until it turned to a clear solution to obtain amidoether derivative mixture 10 shown in Table 1.

COMPARATIVE EXAMPLE 2

Synthesis of Sodium Salt of Amidoether Carboxylic Acid Containing no Amidoether:

After obtaining the carboxymethylized mixture in the same manner as in Example 1, the reaction mixture was added with ethanol to precipitate a solid. Thereafter, it was filtered, and the filter cake was washed with ethanol to remove amidoetether. Further, after the product was made into an acid form as in Example 1, it was neutralize with a 30% sodium hydroxide solution thereby to obtain the amidoether derivative mixture 8 shown in Table 1.

COMPARATIVE EXAMPLE 3

Synthesis of Sodium Salt of Amidoether Carboxylic Acid Containing Amidoether

Amidoether was obtained in the same manner as in Example 1, and the amidoether was reacted with SMCA and solid sodium hydroxide under the condition that 0.05 mol of SMCA and 0.05 mol of solid sodium hydroxide were added per mol of the amidoether. Thereafter the reaction mixture was treated in the same manner as in Example 1 thereby to obtain the amidoether derivative mixture 9 shown in Table 1.

TABLE 1

| Sample | Compound (1) | Compound (2) | Proportion based on Solids Content (% by weight) | | | | | |
|---|---|---|---|---|---|---|---|---|
| | | | (1) | (2) | (1) + (2) | (3) | Others* | (1):(2) |
| Amidoether Derivative Mixture 1 | $R^1$: $C_{11}H_{23}$<br>$R^2$: H<br>M: Na<br>n: 1 | $R^1$: $C_{11}H_{23}$<br>$R^3$: H<br>n: 1 | 91 | 7 | 98 | 0 | 2 | 93:7 |
| Amidoether Derivative Mixture 2 | $R^1$: $C_{11}H_{23}$<br>$R^2$: H<br>M: Na<br>n: 3 | $R^1$: $C_{11}H_{23}$<br>$R^3$: H<br>n: 3 | 82 | 14 | 96 | 0 | 4 | 85:15 |
| Amidoether Derivative Mixture 3 | $R^1$: $C_{11}H_{23}$<br>$R^2$: H<br>M: Na<br>n: 5 | $R^1$: $C_{11}H_{23}$<br>$R^3$: H<br>n: 5 | 77 | 18 | 95 | 0 | 5 | 81:19 |
| Amidoether Derivative Mixture 4 | $R^1$: $C_{11}H_{23}$<br>$R^2$: H<br>M: Na<br>n: 3 | $R^1$: $C_{11}H_{23}$<br>$R^3$: H<br>n: 3 | 49 | 12 | 61 | 0 | 39 | 80:20 |
| Amidoether Derivative Mixture 5 | $R^1$: $C_{13}H_{27}$<br>$R^2$: H<br>M: Na<br>n: 6 | $R^1$: $C_{13}H_{27}$<br>$R^3$: H<br>n: 6 | 70 | 23 | 93 | 0 | 7 | 75:25 |

TABLE 1-continued

| Sample | Compound (1) | Compound (2) | (1) | (2) | (1) + (2) | (3) | Others* | (1):(2) |
|---|---|---|---|---|---|---|---|---|
| Amidoether Derivative Mixture 6 | $R^1$: $C_{17}H_{35}$ $R^2$: H M: Na n: 10 | $R^1$: $C_{17}H_{35}$ $R^3$: H n: 10 | 60 | 35 | 95 | 0 | 5 | 63:37 |
| Amidoether Derivative Mixture 7 | $R^1$: $C_{11}H_{23}$ $R^2$: H M: Mg n: 3 | $R^1$: $C_{11}H_{23}$ $R^3$: H n: 3 | 82 | 14 | 96 | 0 | 4 | 85:15 |
| Amidoether Derivative Mixture 8 | $R^1$: $C_{11}H_{23}$ $R^2$: H M: Na n: 3 | $R^1$: $C_{11}H_{23}$ $R^3$: H n: 3 | 96 | <1 | 96 | 0 | 4 | 100:0 |
| Amidoether Derivative Mixture 9 | $R^1$: $C_{11}H_{23}$ $R^2$: H M: Na n: 4 | $R^1$: $C_{11}H_{23}$ $R^3$: H n: 4 | 4 | 90 | 94 | 0 | 6 | 4:96 |
| Amidoether Derivative Mixture 10 | $R^1$: $C_{11}H_{23}$ $-C_{13}H_{27}$ $R^2$ H M: Na n: 3 | $R^1$: $C_{11}H_{23}$ $-C_{13}H_{27}$ $R^3$: H n: 3 | 23 | 25 | 48 | 30 | 22 | 46:52 |

Note:
*Sodium chloride, glycolic acid salts, etc.

EXAMPLES 8 TO 11 AND COMPARATIVE EXAMPLES 4 TO 9

Detergent compositions (pH 6.5) having the formulation shown in Table 2 below were prepared and evaluated in terms of foam volume, foam quality, touch of hair, and skin irritation according to the following methods. The results obtained are shown in Table 2.

The weight percents of the formulations given in Table 2 are for the effective content of the active agent (solids content as to amidoether carboxylic acid salts). The pH adjustment was conducted by using an aqueous sodium hydroxide solution and citric acid.

Method of Evaluation:

The foam volume, foam quality, and touch of hair were scored by 20 specialized panel members according to standards A given below and judged from the average of 20 scores according to standards B. One gram of a test detergent composition was applied to 20 g of hairs (length: 15 cm) of a healthy Japanese female and made to lather for 1 minute. At this point, the foam volume and foam quality were evaluated. The touch of hair was evaluated at the 1 minute's lathering, at the time of rinsing, and after drying the hair with a hair drier. The results of the evalutaion are shown in Table 2.

Separately, a test detergent composition was applied to the healthy skin of 5 guinea pigs 4 times. The response after the 4th application was scored according to standards A, and the skin irritation was judged from the average of 5 scores according to standards B. The results of the evaluation are shown in Table 2.

(1) Foam volume
A. Standards of evaluation
  Very good lathering . . . 4
  Good lathering . . . 3
  Slightly poor lathering . . . 2
  Poor lathering . . . 1
B. Standards of judgement
  Average score of 3.5 to 4.0 . . . excellent
  Average score of 2.5 to 3.4 . . . good
  Average score of 1.5 to 2.4 . . . fair
  Average score of 1.0 to 1.4 . . . poor
(2) Foam quality
A. Standards of evaluation
  Creamy and very slippery . . . 4
  Creamy and slippery . . . 3
  Slightly coarse and slightly lacking in slipperiness . . . 2
  Coarse and non-slippery . . . 1
B. Standards of judgement
  Average score of 3.5 to 4.0 . . . excellent
  Average score of 2.5 to 3.4 . . . good
  Average score of 1.5 to 2.4 . . . fair
  Average score of 1.0 to 1.4 . . . poor
(3) Touch of hair on lathering
A. Standards of evaluation
  Smooth and soft. . . 4
  Not squeaky and smooth for running fingers through . . . 3
  Slightly rough for running fingers through . . . 2
  Very rough for running fingers through . . . 1
B. Standards of judgement
  Average score of 2.5 to 3.0 . . . good
  Average score of 1.5 to 2.4 . . . fair
  Average score of 1.0 to 1.4 . . . poor
(4) Touch of hair during rinsing
A. Standards of evaluation
  Smooth and soft . . . 4
  Not rough and smooth . . . 3
  Slightly rough and slightly poor in smoothness . . . 2
  Very rough . . . 1
B. Standards of judgement
  Average score of 3.1 to 4.0 . . . excellent
  Average score of 2.5 to 3.0 . . . good Average score of 1.5 to 2.4 . . . fair Average score of 1.0 to 1.4 . . . poor (5) Touch of hair after drying A. Standard of evaluation Smooth and soft . . . 4

Smooth and easy for running fingers through . . . 3

Slightly poor in smoothness and easiness for running fingers through . . . 2

Poor in smoothness for running fingers through . . . 1

B. Standards for judgement

Average score of 3.1 to 4.0 . . . excellent

Average score of 2.5 to 3.0 . . . good

Average score of 1.5 to 2.4 . . . fair

Average score of 1.0 to 1.4 . . . poor (6) Skin irritation

A. Standards of evaluation

Non-irritating (no response observed) . . . 5

Faintly irritating (slight erythema observed) . . . 4

Weakly irritating (obvious erythema observed) . . . 3

Medium-irritating (obvious erythema accompanied by edema) . . . 2

Strongly irritating (obvious erythema accompanied by necrosis or syncope) . . . 1

B. Standards of judgement

Average score of 3.5 to 5.0 . . . good

Average score of 2.5 to 3.4 . . . fair

Average score of 1.0 to 2.4 . . . poor

EXAMPLE 12

A conditioning shampoo having the following formulation and a pH of 6 was prepared. The shampoo was low-irritant to the skin and excellent in foaming properties, foam quality, and touch during shampoo.

| Formulation: | |
|---|---|
| Amidoether derivative mixture | 14% |
| Sodium polyoxyethylene(3) lauryl ether sulfate | 5% |
| Lauric diethanolamide | 3% |
| Cationic gum guaiac (Jaguar C-13-S, produced by Celanese-Stein Hall) | 0.5% |
| Ethylene glycol distearate | 3% |
| Citric acid | adequate amount |
| Sodium hydroxide | adequate amount |
| Perfume | 0.2% |
| Ion-exchanged water | balance |

EXAMPLE 13

A body shampoo having the following formulation and a pH of 5.5 was prepared. The body shampoo was low-irritant to the skin and excellent in foaming properties and foam quality, and gives the skin smooth touch after washing.

| Formulation: | |
|---|---|
| Amidoether derivative mixture 6 | 10% |
| Sodium polyoxyethylene(4.5) lauryl ether acetate (Akypo RLM45, produced by Chem Y) | 10% |

TABLE 2

| | (% by weight) | | | | | | | | | |
|---|---|---|---|---|---|---|---|---|---|---|
| | Examples | | | | Comparative Examples | | | | | |
| | 8 | 9 | 10 | 11 | 4 | 5 | 6 | 7 | 8 | 9 |
| Amidoether Derivative Mixture 1 | 10 | — | 10 | — | — | — | — | — | — | — |
| Amidoether Derivative Mixture 2 | — | 10 | — | — | 10 | — | — | — | — | — |
| Amidoether Derivative Mixture 7 | — | — | — | 10 | — | — | — | — | — | — |
| Amidoether Derivative Mixture 8 | — | — | — | — | — | 10 | — | — | — | — |
| Amidoether Derivative Mixture 9 | — | — | — | — | — | — | 10 | — | — | — |
| Amidoether Derivative Mixture 10 | — | — | — | — | — | — | — | 10 | — | 20 |
| Disodium Polyoxyethylene (4) Lauryl Ether Sulfosuccinate | — | — | — | — | — | — | — | — | 10 | — |
| Cationic Polymer 1*[1] | 0.5 | 0.3 | — | 0.2 | — | — | 0.2 | 0.5 | 0.5 | 0.3 |
| Cationic Polymer 2*[2] | — | — | 0.2 | — | — | — | — | — | — | — |
| Ion-exchanged Water | Balance | Balance | Balance | Balance | Balance | Balance | Balance | Balance | Balance | Balance |
| Evaluation | | | | | | | | | | |
| Foam Volume | Excellent | Excellent | Excellent | Excellent | Good | Poor | Poor | Poor | Poor | Poor |
| Foam Quality | Excellent | Excellent | Excellent | Excellent | Fair | Fair | Poor | Poor | Poor | Poor |
| Touch on Lathering | Good | Good | Good | Good | Fair | Fair | Fair | Good | Fair | Good |
| Touch on Rinsing | Good | Good | Good | Excellent | Poor | Poor | Fair | Good | Fair | Good |
| Touch of Hair after Drying | Good | Good | Good | Excellent | Poor | Poor | Fair | Good | Poor | Good |
| Skin Irritation | Good | Good | Good | Good | Good | Good | Good | Good | Good | Good |

Note:

*[1] Cationic cellulose (Polymer JR-400, produced by Union Carbide Corp.)

*[2] (Dimethyldiallylammonium chloride/acrylamide) copolymer (Mercoat-550., produced by Merck & Co., Inc.)

-continued

| Formulation: | |
|---|---|
| Cationic polymer (Gaffcoat, produced by Gaff Corp.; vinylpyrrolidone/dimethylamino-ethyl acrylate copolymer quaternarized with ethylsulfate) | 0.3% |
| Citric acid | adequate amount |
| Sodium hydroxide | adequate amount |
| Perfume | 0.2% |
| Ion-exchanged water | balance |

EXAMPLE 14

An antidandruff shampoo having the following formulation and a pH of 6.5 was prepared. The shampoo was low-irritant to the skin and excellent in antidandruff effects, foaming properties, and touch of the hair after shampoo.

| Formulation: | |
|---|---|
| Amidoether derivative mixture 4 | 15% |
| Ammonium laurylsulfate | 5% |
| Cationic cellulose (Polymer JR-400, produced by Union Carbide Corp.) | 0.3% |
| Zinc Pyrithione | 1% |
| Carboxyvinyl polymer (Carbopole 941, produced by Goodrich Corp.) | 0.5% |
| Citric acid | adequate amount |
| Sodium hydroxide | adequate amount |
| Perfume | 0.2% |
| Ion-exchanged water | balance |

EXAMPLE 15

A dish-washing detergent having the following formulation and a pH of 6 was prepared. The detergent was low-irritant to the skin and excellent in detergency, foaming properties, foam quality, and touch of the hands after dish washing.

| Formulation: | |
|---|---|
| Amidoether derivative mixture 1 | 15% |
| Laurylamine oxide | 4% |
| Lauric diethanolamide | 2% |
| Cationic polymer (Mercoat 280, produced by Merck & Co., Inc.; dimethyldiallylammonium chloride/acrylic acid copolymer) | 0.1% |
| Citric acid | adequate amount |
| Sodium hydroxide | adequate amount |
| Ethanol | 3% |
| Perfume | 0.2% |
| Ion-exchanged water | balance |

EXAMPLE 16

A conditioning shampoo having the following formulation and a pH of 6.7 was prepared. The shampoo was low-irritant to the skin and excellent in foaming properties, foam quality, and touch of hair during rinsing and after drying.

| Formulation: | |
|---|---|
| Amidoether derivative mixture 3 | 15% |
| Cationic polymer (Mercoat 100, produced by Merck & Co., Inc.; dimethyldiallylammonium chloride polymer) | 0.2% |
| Lauric diethanolamide | 4% |
| Citric acid | adequate amount |
| Perfume | adequate amount |
| Ion-exchanged water | balance |

EXAMPLE 17

A conditioning shampoo having the following formulation and a pH 7.0 was prepared. The shampoo was low-irritant to the skin and excellent in foaming properties and foam quality, and particularly excellent in touch of hair during rinsing and after drying.

| Formulation: | |
|---|---|
| Amidoether derivative mixture 7 | 15% |
| Cationic cellulose (Polymer JR, produced by Union Carbide Corp.) | 1% |
| Laurylamine oxide | 4% |
| Lactic Acid | adequate amount |
| Sodium hydroxide | adequate amount |
| Perfume | 0.1% |
| Ion-exchanged water | balance |

EXAMPLE 18

A conditioning shampoo having the following formulation and a pH of 7.0 was prepared. The shampoo was low-irritant to the skin and excellent in foaming properties, foam quality, and touch of hair during rinsing and after drying.

| Formulation: | |
|---|---|
| Amidoether derivative mixture 7 | 15% |
| Cationic polymer (Mercoat 100, produced by Merck & Co., Inc.; dimethyldiallylammonium chloride polymer) | 0.5% |
| Coconut fatty oil acid diethanolamide | 4% |
| Citric acid | adequate amount |
| Sodium hydroxide | adequate amount |
| Perfume | 0.1% |
| Ion-exchanged Water | balance |

EXAMPLES 19 TO 22 AND COMPARATIVE EXAMPLES 10 TO 15

Detergent compositions (pH 6.5) having the formulations shown in Table 3 were prepared and evaluated in terms of foam volume, foam quality, touch of hair, and skin irritation according to the following methods. The results obtained are shown in Table 3.

The weight percents of the formulations given in Table 3 are for the effective content of the active agent (solids content as to amidoether carboxylic acid salts). The pH adjustment was conducted by using an aqueous sodium hydroxide solution and citric acid.

Method of Evaluation

The foam volume, gloss of hair after drying, and smoothness of running a comb through hair after drying were scored by 20 specialized panel members according to standards A given below and judged from the average of 20 scores according to standards B. One gram of a test detergent composition was applied to 20 g of hairs (length: 15 cm) of B. Standards of judgement
Average score of 2.5 to 3.0 ... good
Average score of 1.5 to 2.4 ... fair
Average score of 1.0 to 1.4 ... poor

TABLE 3

| | (% by weight) | | | | | | | | | |
|---|---|---|---|---|---|---|---|---|---|---|
| | Examples | | | | Comparative Examples | | | | | |
| | 19 | 20 | 21 | 22 | 10 | 11 | 12 | 13 | 14 | 15 |
| Amidoether Derivative Mixture 1 | 10 | — | 10 | — | — | — | — | — | — | — |
| Amidoether Derivative Mixture 2 | — | 10 | — | — | 10 | — | — | — | — | — |
| Amidoether Derivative Mixture 7 | — | — | — | 10 | — | 10 | — | — | — | — |
| Amidoether Derivative Mixture 8 | — | — | — | — | — | 10 | — | — | — | — |
| Amidoether Derivative Mixture 9 | — | — | — | — | — | — | 10 | — | — | — |
| Amidoether Derivative Mixture 10 | — | — | — | — | — | — | — | 10 | — | 20 |
| Disodium Polyoxyethylene (3) Lauryl Ether Sulfosuccinate | — | — | — | — | — | — | — | — | 10 | — |
| Dimethylpolysiloxane (100,000 cs) | 0.5 | — | — | 1 | — | — | — | — | 0.7 | — |
| Polyether-modified Silicone*[1] | — | 2 | — | — | — | 1 | — | 2 | — | 3 |
| Amino-modified Silicone Emulsion*[2] | — | — | 2 | — | — | — | 1 | — | — | — |
| Ion-exchanged Water | Balance | Balance | Balance | Balance | Balance | Balance | Balance | Balance | Balance | Balance |
| Evaluation | | | | | | | | | | |
| Foam Volume | Good | Good | Good | Good | Good | Poor | Poor | Poor | Poor | Poor |
| Hair Gloss after Drying | Good | Good | Good | Good | Fair | Fair | Fair | Poor | Fair | Poor |
| Smoothness in Running a Comb after Drying | Good | Good | Good | Good | Poor | Fair | Fair | Fair | Fair | Fair |
| Skin Irritation | Good | Good | Good | Good | Good | Good | Good | Good | Good | Good |

Note:
*[1]KF352 (A), produced by Shin-Etsu Chemical Co., Ltd.
*[2]SM6702C, produced by Toray Sillicone Co., Ltd.

a healthy Japanese female and made to lather for 1 minute. At this point, the foam volume was evaluated. The smoothness of running a comb through hair was evaluated after drying the hair with a hair drier.

The skin irritation was evaluated and judged in the same manner as in Example 8.

(1) Foam volume

A. Standards of evaluation

Good lathering ... 3

Slightly poor lathering ... 2

Poor lathering ... 1

B. Standards of judgement

Average score of 2.5 to 3.0 ... good

Average score of 1.5 to 2.4 ... fair

Average score of 1.0 to 1.4 ... poor (2) Gloss of hair after drying

A. Standards of evaluation

Glossy ... 3

Slightly lacking in gloss ... 2

Lacking in gloss ... 1

B. Standards of judgement

Average score of 2.5 to 3.0 ... good

Average score of 1.5 to 2.4 ... fair

Average score of 1.0 to 1.4 ... poor (3) Smoothness in running a comb through hair after drying A. Standards of evaluation Smooth in running a comb ... 3

Slightly rough in running a comb ... 2

Not smooth in running a comb ... 1

EXAMPLE 23

A conditioning shampoo having the formulation shown below and having a pH of 5.9 was prepared. The shampoo was low-irritant to the skin and excellent in foaming properties, foam quality, hair gloss after drying, and smoothness in running a comb through the hair after drying.

| Formulation: | |
|---|---|
| Amidoether derivative mixture 2 | 14% |
| Sodium polyoxyethylene(2) lauryl ether sulfate | 5% |
| Lauric diethanolamide | 3% |
| Dimethylpolysiloxane (KF96 (5000 cst), produced by Shin-Etsu Chemical Co., Ltd.) | 0.5% |
| Polyether-modified silicone (KF945A, produced by Shin-Etsu Chemical Co., Ltd.) | 3% |
| Citric acid | adequate amount |
| Sodium hydroxide | adequate amount |
| Perfume | 0.2% |
| Ion-exchanged water | balance |

EXAMPLE 24

Facial cleansing foam having the following formulation and a pH of 6.8 was prepared. The foam was low-irritant to the skin and excellent in foaming properties, foam quality, and skin smoothness after facial cleansing.

| Formulation: | |
|---|---|
| Amidoether derivative mixture 4 | 10% |
| Coconut fatty acid methyltaurine sodium salt | 5% |
| Polyether-modified silicone (SH3772C, produced by Toray Silicone Co., Ltd.) | 0.3% |

| Formulation: | |
|---|---|
| Citric acid | adequate amount |
| Sodium hydroxide | adequate amount |
| Perfume | 0.1% |
| Ion-exchanged water | balance |

EXAMPLE 25

A conditioning type liquid body soap having the following formulation adjusted to pH 6.9 was prepared. The body soap was low-irritant to the skin and excellent in foaming properties, foam quality and smoothness of the skin after washing.

| Formulation: | |
|---|---|
| Amidoether derivative mixture 5 | 10% |
| Amidoether derivative mixture 6 | 5% |
| Sodium polyoxyethylene lauryl ether acetate (Akypo RLM100, produced by Chem Y) | 5% |
| Dimethylpolysiloxane (2,000,000 cst) | 1% |
| Ethylene glycol monostearate | 2% |
| Hydroxyethyl cellulose | 0.5% |
| Citric acid | adequate amount |
| Sodium hydroxide | adequate amount |
| Perfume | 0.1% |
| Ion-exchanged water | balance |

EXAMPLE 26

A conditioning shampoo having the following formulation and a pH of 6.5 was prepared. The shampoo was excellent in foaming properties, foam quality, and conditioning effects on the hair after shampoo and drying, i.e., hair gloss, smoothness in running a comb through, and easiness in doing the hair.

| Formulation: | |
|---|---|
| Amidoether derivative mixture 3 | 10% |
| Ammonium laurylsulfate | 8% |
| Lauric diethanolamide | 2% |
| Amino-modified silicone emulsion (DC929, produced by Dow Corning Corp.) | 0.5% |
| Hydrolyzed collagen | 0.5% |
| Citric acid | adequate amount |
| Sodium hydroxide | adequate amount |
| Perfume | 0.1% |
| Ion-exchanged water | balance |

EXAMPLE 27

A dish-washing detergent having the following formulation and a pH of 6.2 was prepared. The detergent was low-irritant to the skin and excellent in detergency, foaming properties, foam quality, and touch of the hands after dish-washing.

| Formulation: | |
|---|---|
| Amidoether derivative mixture 1 | 15% |
| Laurylamine oxide | 4% |
| Lauric diethanolamide | 2% |
| Polyether-modified silicone (KF352(A), produced by Shin-Etsu Chemical Co., Ltd.) | 0.5% |

| Formulation: | |
|---|---|
| Carboxyvinyl polymer | 0.3% |
| Citric acid | adequate amount |
| Sodium hydroxide | adequate amount |
| Perfume | 0.2% |
| Ion-exchanged water | balance |

EXAMPLE 28

A conditioning shampoo having the following formulation and a pH of 6.3 was prepared. The shampoo was low-irritant to the skin and excellent in foaming properties, foam quality, and in hair gloss, smoothness in running a comb through, and easiness in doing the hair during and after shampoo.

| Formulation: | |
|---|---|
| Amidoether derivative mixture 7 | 21% |
| Coconut oil fatty acid diethanol amide | 3% |
| Dimethylpolysiloxane (3,000,000 cst) | 1% |
| Citric acid | adequate amount |
| Sodium hydroxide | adequate amount |
| Perfume | 0.3% |
| Ion-exchanged Water | balance |

EXAMPLE 29

A conditioning shampoo having the following formulation and a pH of 7.1 was prepared. The shampoo was low-irritant to the skin and excellent in foaming properties, foam quality, and in hair gloss, smoothness in running a comb through, and easiness in doing the hair during and after shampoo.

| Formulation: | |
|---|---|
| Amidoether derivative mixture 7 | 17% |
| Lauric diethanolamide | 4% |
| Polyether-modified silicone (SH3772C, produced by Toray Silicone Co., Ltd.) | 2% |
| Lactic acid | adequate amount |
| Sodium hydroxide | adequate amount |
| Perfume | 0.3% |
| Ion-exchanged water | balance |

EXAMPLE 30

A conditioning shampoo having the following formulation and a pH of 7.1 was prepared. The shampoo was low-irritant to the skin and excellent in foaming properties, foam quality, and in hair gloss, smoothness in running a comb through, and easiness in doing the hair during and after shampoo.

| Formulation: | |
|---|---|
| Amidoether derivative mixture 7 | 17% |
| Laurylamine oxide | 4% |
| Amino-modified silicone emulsion (SM8704C, | 1% |

| Formulation: | |
|---|---|
| produced by Toray Silicone Co., Ltd.) | |
| Lactic acid | adequate amount |
| Sodium hydroxide | adequate amount |
| Perfume | 0.5% |
| Ion-exchanged water | balance |

EXAMPLES 31 TO 35 AND COMPARATIVE EXAMPLES 16 TO 22

Detergent compositions (pH 6.5) having the formulations shown in Table 4 below were prepared and evaluated in terms of foam volume, foam quality, touch of hair after shampoo, and skin irritation in the same manner as in Example 8. The results obtained are shown in Table 4.

| Formulation: | |
|---|---|
| Citric acid | adequate amount |
| Sodium hydroxide | adequate amount |
| Ion-exchanged water | balance |

EXAMPLE 37

A conditioning type liquid body soap having the following formulation and a pH of 6.5 was prepared. The body soap was low-irritant to the skin and excellent in foaming properties, foam quality and smoothness of the skin after washing.

TABLE 4

| | (% by weight) | | | | | | | | | | | |
|---|---|---|---|---|---|---|---|---|---|---|---|---|
| | Examples | | | | | Comparative Examples | | | | | | |
| | 31 | 32 | 33 | 34 | 35 | 16 | 17 | 18 | 19 | 20 | 21 | 22 |
| Amidoether Derivative Mixture 1 | 10 | — | 10 | — | — | — | — | — | — | — | — | — |
| Amidoether Derivative Mixture 2 | — | 10 | — | 10 | — | 10 | — | — | — | — | — | — |
| Amidoether Derivative Mixture 7 | — | — | — | — | 10 | — | — | — | — | — | — | — |
| Amidoether Derivative Mixture 8 | — | — | — | — | — | — | 10 | — | — | — | — | — |
| Amidoether Derivative Mixture 9 | — | — | — | — | — | — | — | 10 | — | — | — | 10 |
| Amidoether Derivative Mixture 10 | — | — | — | — | — | — | — | — | 10 | — | 20 | — |
| Sodium Polyoxyethylene (4.5) Lauryl Ether Acetate*[1] | — | — | — | — | — | — | — | — | — | 10 | — | — |
| Monostearyltrimethylammonium Chloride | 0.3 | — | — | — | 0.2 | — | — | — | — | 0.1 | — | — |
| Dialkyldimethylammonium Chloride*[2] | — | 0.3 | — | — | — | — | — | — | 0.3 | — | 0.2 | — |
| 2-Dodecylhexadecyltrimethyl-ammonium Chloride | — | — | 0.2 | — | — | — | — | 0.2 | — | — | — | — |
| Stearic Dimethylaminopropylamide | — | — | — | 0.3 | — | — | — | — | — | — | — | 0.4 |
| Ion-exchanged Water | Balance | Balance | Balance | Balance | Balance | Balance | Balance | Balance | Balance | Balance | Balance | Balance |
| Evaluation | | | | | | | | | | | | |
| Foam Volume | Good | Good | Good | Good | Good | Good | Poor | Poor | Poor | Poor | Poor | Poor |
| Foam Quality | Excellent | Excellent | Excellent | Excellent | Excellent | Fair | Fair | Poor | Poor | Poor | Poor | Poor |
| Touch on Lathering | Good | Good | Good | Good | Good | Fair | Fair | Fair | Poor | Poor | Poor | Fair |
| Touch on Rinsing | Good | Good | Good | Good | Good | Poor | Poor | Fair | Poor | Fair | Poor | Fair |
| Touch of Hair after Drying | Good | Good | Good | Good | Good | Poor | Poor | Fair | Poor | Poor | Poor | Fair |
| Skin Irritation | Good | Good | Good | Good | Good | Good | Good | Good | Good | Good | Good | Good |

Note:
*[1] A neutralized product of Akypo RLM45 (produced by Chem Y)
*[2] Branched quaternary ammonium salt derived from a commercially available oxo alcohol having 12 to 15 carbon atoms (an equal volume mixture of Dovanol 23 and Dovanol 45, produced by Mitsubishi Petrochemical Co., Ltd.); branching ratio: 20% by weight.

EXAMPLE 36

A conditioning shampoo having the following formulation and a pH of 5.9 was prepared. The shampoo was low-irritant to the skin and excellent in foaming properties, foam quality, and touch of hair during and after shampoo.

| Formulation: | |
|---|---|
| Amidoether derivative mixture 2 | 14% |
| Sodium polyoxyethylene(2) lauryl ether sulfate | 5% |
| Coconut fatty acid diethanolamide | 2% |
| 2-Decyltetradecyltrimethylammonium chloridE | 0.2% |
| Perfume | 0.2% |

| Formulation: | |
|---|---|
| Amidoether derivative mixture 4 | 10% |
| Sodium lauroylmethyltaurine | 5% |
| 2-Octyldodecyltrimethylammonium chloride | 0.2% |
| Perfume | 0.1% |
| Citric acid | adequate amount |
| Sodium hydroxide | adequate amount |
| Ion-exchanged water | balance |

EXAMPLE 38

A conditioning type liquid body soap having the following formulation and a pH of 5.7 was prepared. The body soap was low-irritant to the skin and excellent in foaming properties, foam quality and smoothness of the skin after washing.

| Formulation: | |
| --- | --- |
| Amidoether derivative mixture 6 | 10% |
| Sodium polyoxyethylene lauryl ether acetate (Akypo RLM, produced by Chem Y) | 5% |
| Monostearyltrimethylammonium chloride | 0.2% |
| Ethylene glycol monostearate | 2% |
| Hydroxyethyl cellulose | 0.3% |
| Perfume | 0.2% |
| Citric acid | adequate amount |
| Sodium hydroxide | adequate amount |
| Ion-exchanged water | balance |

EXAMPLE 39

A conditioning shampoo having the following formulation and a pH of 6.6 was prepared. The shampoo was excellent in foaming properties, foam quality, and conditioning effects on the hair after shampoo and drying, i.e., hair gloss, smoothness in running a comb through, and easiness in doing the hair.

| Formulation | |
| --- | --- |
| Amidoether derivative mixture 3 | 10% |
| Ammonium polyoxyethylene(2) lauryl ether sulfate | 6% |
| Lauric diethanolamide | 2% |
| Monocetyltrimethylammonium chloride | 0.3% |
| Perfume | 0.1% |
| Citric acid | adequate amount |
| Sodium hydroxide | adequate amount |
| Ion-exchanged water | balance |

EXAMPLE 40

A dish-washing detergent having the following formulation and a pH of 6.5 was prepared. The detergent was low-irritant to the skin and excellent in detergency, foaming properties, foam quality, and touch of the hands after dish-washing.

| Formulation: | |
| --- | --- |
| Amidoether derivative mixture 1 | 15% |
| Laurylamine oxide | 4% |
| Lauric diethanolamide | 2% |
| Dialkyldimethylammonium chloride [branched quaternary ammonium salt derived from a commercially available oxo alcohol having 12 to 15 carbon atoms (an equal volume mixture of Dovanol 23 and Dovanol 45, produced by Mitsubishi Petrochemical Co., Ltd.); branching ratio: 20% by weight] | 0.1% |
| Carboxyvinyl polymer | 0.3% |
| Perfume | 0.2% |
| Carboxyvinyl polymer | 0.3% |
| Citric acid | adequate amount |
| Sodium hydroxide | adequate amount |
| Ion-exchanged water | balance |

EXAMPLE 41

A conditioning shampoo having the following formation and a pH of 6.9 was prepared. The shampoo was low-irritant to the skin and excellent in foaming properties, foam quality, and touch of hair during and after shampoo.

| Formulation: | |
| --- | --- |
| Amidoether derivative mixture 7 | 12% |
| Sodium polyoxyethylene (3) lauryl ether sulfate | 5% |
| Stearic dimethylaminopropylamide | 0.3% |
| Perfume | 0.1% |
| Citric acid | adequate amount |
| Sodium hydroxide | adequate amount |
| Ion-exchanged water | balance |

EXAMPLE 42

A conditioning shampoo having the following formation and a pH of 6.7 was prepared. The shampoo was low-irritant to the skin and excellent in foaming properties, foam quality, and touch of hair during and after shampoo.

| Formulation: | |
| --- | --- |
| Amidoether derivative mixture 7 | 17% |
| Laurylamine oxide | 4% |
| Monostearyltrimethylammonium chloride | 0.5% |
| Ethylene glycol monostearate | 2% |
| Citric acid | adequate amount |
| Sodium hydroxide | adequate amount |
| Perfume | 0.3% |
| Ion-exchanged water | balance |

EXAMPLE 43

A conditioning shampoo having the following formation and a pH of 6.1 was prepared. The shampoo was low-irritant to the skin and excellent in foaming properties, foam quality, and touch of hair during and after shampoo.

| Formulation: | |
| --- | --- |
| Amidoether derivative mixture 7 | 17% |
| Coconut fatty oil diethenolamide | 4% |
| Stearic acid dimethylaminopropylamide | 1% |
| Citric acid | adequate amount |
| Sodium hydroxide | adequate amount |
| Perfume | 0.3% |
| Ion-exchanged water | balance |

EXAMPLE 44

A conditioning shampoo having the following formation and a pH of 6.5 was prepared. The shampoo was low-irritant to the skin and excellent in foaming properties, foam quality, and touch of hair during rinsing and after drying.

| Formulation: | |
| --- | --- |
| Amidoether derivative mixture 2 | 15% |
| Decyl polyglycoside (degree of polymerization of glucose: 1.5) | 5% |
| Cationic cellulose (Polymer JR-400, produced by Union Carbide Corp.) | 1% |
| Citric acid | adequate amount |
| Sodium hydroxide | adequate amount |
| Perfume | 0.1% |
| Ion-exchanged water | balance |

EXAMPLE 45

A conditioning shampoo having the following formation and a pH of 7.0 was prepared. The shampoo was low-irritant to the skin and excellent in foaming properties, foam quality, and touch of hair during rinsing and after drying.

| Formulation: | |
|---|---|
| Amidoether derivative mixture 5 | 13% |
| Decyl polyglycoside | 6% |
| (degree of polymerization of glucose: 1.5) | |
| Cationic polymer | 0.5% |
| (Mercoat 100, produced by Merck & Co., Inc.; dimethyldiallylammonium chloride polymer) | |
| Coconut fatty acid diethanolamide | 2% |
| Citric acid | adequate amount |
| Sodium hydroxide | adequate amount |
| Perfume | 0.1% |
| Ion-exchanged water | balance |

EXAMPLE 46

A conditioning shampoo having the following formation and a pH of 6.5 was prepared. The shampoo was low-irritant to the skin and excellent in foaming properties, foam quality, and hair gloss after drying, and smoothness in running a comb through the hair after washing and drying.

| Formulation: | |
|---|---|
| Amidoether derivative mixture 4 | 17% |
| Decyl polyglycoside | 4% |
| (degree of polymerization of glucose: 1.1) | |
| Dimethylpolysiloxane (4,000,000 cst) | 2% |
| Hyderoxyethyl cellulose | 1% |
| Citric acid | adequate amount |
| Sodium hydroxide | adequate amount |
| Perfume | 0.1% |
| Ion-exchanged water | balance |

EXAMPLE 47

A conditioning shampoo having the following formation and a pH of 7.2 was prepared. The shampoo was low-irritant to the skin and excellent in foaming properties, foam quality, and touch of hair during shampooing and after washing.

| Formulation: | |
|---|---|
| Amidoether derivative mixture 3 | 10% |
| Decyl polyglycoside | 6% |
| (degree of plymerization of glucose: 1.7) | |
| Monocetyltrimethylammonium chloride | 0.1% |
| Stearic dimethylaminopropylamide | 0.3% |
| Citric acid | adequate amount |
| Sodium hydroxide | adequate amount |
| Perfume | 0.3% |
| Ion-exchanged water | balance |

What is claimed is:

1. A detergent composition comprising components (A) and (B):

wherein (A) is an amidoether derivative mixture comprising:

(i) an amidoether carboxylic acid or a salt thereof represented by formula (1).

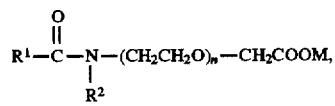
(1)

(ii) an amidoether represented by formula (2).

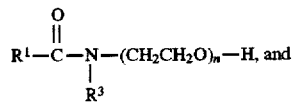
(2)

(iii) a glycerin derivative represented by formula (3);

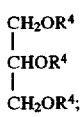
(3)

wherein $R^1$ represents a straight-chain or branch alkyl or alkenyl group having 7 to 17 carbon atoms or a phenyl group substituted with an alkyl group having 7 to 17 carbon atoms;

$R^2$ represents a hydrogen atom or an alkyl group having 1 to 3 carbon atoms;

M represents a hydrogen atom, an alkali metal, an alkaline earth metal, an ammonium group, an alkanolamine or a basic amino acid;

n and m, which may be the same or different, each represent a number of from 1 to 10;

$R^3$ represents a hydrogen atom, or an alkyl group having 1 to 3 carbon atoms; and $R^4$ represents a hydrogen atom, —$(CH_2CH_2O)_nCH_2COOM$ or —$(CH_2CH_2O)_mH$;

in which $R^1$, M, n, and m in formulae (1), (2) and (3) may be the same or different; wherein the total amount of the amidoether carboxylic acid or a salt thereof (1) and the amidoether (2) is 50% by weight or more based on the solid content of the amidoether derivative mixture (A);

the weight ratio of the amidoether carboxylic acid or a salt thereof (1) to the amidoether (2) is from 95:5 to 60:40; and the amount of the glycerin derivative (3) is 5% by weight or less based on the solid content of the amidoether derivative mixture (A), and wherein (B) is a conditioning component which is at least one member selected from the group consisting of a cationic polymer, a silicone, a silicone derivative, a quaternary ammonium salt, and a tertiary amine other than (1) and (2), and wherein the amounts of the amidoether derivative mixture (A) and the conditioning component (B) are from 5 to 50% by weight and from 0.01 to 10% by weight, respectively, based on the total amount of the detergent composition.

2. The detergent composition according to claim 1, wherein (B) is a cationic polymer.

3. The detergent composition according to claim 1, wherein (B) is a silicone.

4. The detergent composition according to claim 1, wherein (B) is a silicone derivative.

5. The detergent composition according to claim 1, wherein (B) is a quaternary ammonium salt.

6. The detergent composition according to claim 1, wherein (B) is a tertiary amine other than (1) and (2).

7. The detergent composition according to claim 1, wherein the quaternary ammonium salt is a branched quaternary ammonium salt.

8. The detergent composition according to claim 1, wherein the tertiary amine is an amidoamine.

9. The detergent composition according to claim 1, wherein the total amount of the amidoether carboxylic acid or a salt thereof (1) and the amidoether (2) is 60% by weight or more based on the solid content of the amidoether derivative mixture (A);

the weight ratio of the amidoether carboxylic acid or a salt thereof (1) to the amidoether (2) is from 95:5 to 60:40; and the amount of the glycerin derivative (3) is 3% by weight or less based on the solid content of the amidoether derivative mixture (A).

10. The detergent composition according to claim 1, wherein the component (A) is obtained by preparing a fatty acid alkanolamide synthesized from a fatty acid lower alcohol ester.

11. The detergent composition according to claim 1, wherein the detergent composition has a pH of from 4 to 7.

* * * * *